United States Patent [19]

Tsumura et al.

[11] Patent Number: 4,684,256

[45] Date of Patent: Aug. 4, 1987

[54] APPARATUS AND METHOD FOR CONTINUOUSLY MEASURING POLARIZING PROPERTY

[75] Inventors: Akio Tsumura; Suguru Yamamoto; Chiharu Miyaake, all of Osaka, Japan

[73] Assignee: Nitto Electric Industrial Co., Ltd., Osaka, Japan

[21] Appl. No.: 687,403

[22] Filed: Dec. 28, 1984

[30] Foreign Application Priority Data

Dec. 30, 1983 [JP] Japan ............................ 58-248830
Dec. 30, 1983 [JP] Japan ............................ 58-248831
Dec. 30, 1983 [JP] Japan ............................ 58-248832
May 1, 1984 [JP] Japan ............................ 59-88877
May 1, 1984 [JP] Japan ............................ 59-88878

[51] Int. Cl.$^4$ .................................................. G01B 4/00
[52] U.S. Cl. ............................................ 356/367; 356/366
[58] Field of Search ............... 356/366, 367, 31, 33, 356/35

[56] References Cited

U.S. PATENT DOCUMENTS 3,994,593 11/1976 Kato et al. ...................... 356/444
4,469,443 9/1984 Geller ............................. 356/364

OTHER PUBLICATIONS

"Kerr Effect: Application to Phase and Electric Field Induced Absorption Measurements in Glasses", Paillette, *Optics Communications*, 15 Mar. 82, vol. 41, #2.

*Primary Examiner*—R. A. Rosenberger
*Assistant Examiner*—Crystal D. Cooper
*Attorney, Agent, or Firm*—Sughrue, Mion, Zinn, Macpeak & Seas

[57] ABSTRACT

An apparatus for measuring an optical axis direction in which an intensity of the light transmissive to a specimen to be measured disposed between two polarizers is measured by an orthogonal Nicol optical system which uniaxially comprises a light source, said two polarizers, and a light receptor thereby determining the optical axis direction of the specimen to be measured. The apparatus comprises a conveyor for continuously moving the specimen in an elongated form in the direction intersecting with the orthogonal Nicol optical system at a right angle. An intensity of the transmissive light is measured during the period of time when the specimen is fed from one side of a casing, and removed from the other side of the casing. The casing encases the optical system.

8 Claims, 7 Drawing Figures

APPARATUS AND METHOD FOR CONTINUOUSLY MEASURING POLARIZING PROPERTY

BACKGROUND OF THE INVENTION

This invention relates to an apparatus and method for continuously measuring a polarizing property such as an optical axis direction and a light absorbing direction of a polarizing material, and, more particularly, it relates to an apparatus and method for continuously measuring an optical axis direction of a transparent specimen in the respective positions in the longitudinal direction.

For measurement of an optical axis direction of a transparent specimen, as shown in FIG. 1, the prior art has heretofore proposed to employ an orthogonal Nicol optical system which consists of a light source 1, two polarizers 3a, 3b disposed to intersect optical axes thereof with each other, and a light receptor 4 to insert a specimen 2 in a chip form to be measured between both the polarizers 3a, 3b. The surfaces of the specimen intersect with the axis of the optical system at a right angle. The specimen is rotated around the axis of the optical axis, thereby determining the optical axis of the specimen in accordance with a relationship between its rotational angle and an intensity of the light passing through the optical system. If the specimen is elongated and the optical axis direction is varied in the respective positions in the longitudinal direction, such a conventional apparatus is required not only to cut the specimen into segments in a moderate length in order to determine the optical axis direction in the respective positions but also to measure the optical axis direction of every segment. This will cause much labor and time to be consumed.

In the prior art apparatus, as shown in FIG. 1A the apparatus is designed so that a cover 7 is mounted adjacent the holder 5 on a casing 6 which acts to prevent the light from entering from outside, and that the cover 7 is opened to operate the holder for its rotation in measuring. This will render the light easy to enter, thereby causing an inaccurate measurement. This will also require the cover to open and close whenever the holder 5 is rotated, thereby causing difficulty in operation to eventually render measurement insufficient.

Various apparatus have been heretofore proposed and suggested to measure the angle of deviation from the absorption axis of each of various polarizers and to examine quality but failed in providing a desirable apparatus. At the experimental level, an apparatus as shown in FIG. 1B has been well known. More specifically, as seen from FIG. 1B, a polarizer plate 83 as a specimen to be measured is held between two polarizers 81, 82 whose absorption axes are intersected with each other. The light of a fluorescent lamp 84 or the like is transmitted from one side to the polarizers to rotate only the polarizer plate 83 while being observed by the naked eye 84'. When the transmissive light is most lowered, the angle of displacement from the polarizer plate 83 may be obtained by measuring with a protractor an angle defined by one side of the polarizer plate 83 and either one of the polarizers 81, 82. However, as disadvantages derived from the prior art, it is necessary to limit a measurement to one point, it is impossible to conduct a continuous measurement, and it is impossible to conduct a measurement of an accurate and fine angle of displacement.

Also, various methods have been therefore proposed and suggested to measure an angle of displacement or deviation from the absorption axis each of various polarizers but not succeeded in obtaining an established method. Various polarizers are indispensable to a display apparatus, especially, to a display apparatus for use with a liquid crystal. For such application, should an axis of a polarizer be displaced, a transmittivity of visual light is out of a specification limit. Furthermore, a problem of unevenness in color and the like arises from the polarizer assembled into a cell.

SUMMARY OF THE INVENTION

It is an object of the invention to remove defects in the prior art as aforementioned and to provide a measuring apparatus for the optical axis direction, which is capable of continuously measuring the optical axis direction of the elongated specimen in the longitudinal direction and which facilitates feed and removal of the specimen to be measured.

It is another object of the invention is to provide a measuring apparatus for the optical axis direction, which is simple, compact in construction, light in weight.

It is still another object of the present invention to provide a continuous measuring apparatus for optical axis direction which is easy and quick to operate and prevents the light from entering to establish accurate measurement.

It is still another object of the invention to provide an apparatus which is capable of accurately, efficiently measuring the angle of deviation from the absorption axis in the respective positions in the specimen to be measured, such as polarizers or the like and which is easy to handle and compact in structure.

It is still another object of the invention to provide a method for measuring the angle of deviation from the absorption axis in the respective positions of various polarizers and the like.

According to the present invention, there is provide a continuous measuring apparatus for a polarizing property of a specimen, wherein an intensity of the light transmissive to a specimen to be measured disposed between two polarizers is measured by an orthogonal Nicol optical system which comprises a light source, said two polarizers, and a light receptor which are uniaxially arranged, thereby determining the optical axis direction of the specimen to be measured, characterized by conveyor means for continuously moving the specimen in an elongated form to be measured in a direction intersecting with the orthogonal Nicol optical system at a right angle, and in that intensity of the transmissive light is measured during the period of time when the specimen to be measured is fed from the casing, which encircles said optical system, on one side thereof and removed from the other side of the casing.

According to the invention, there is provided a continuous measuring apparatus for an optical axis direction wherein intensity of the light transmissive to a specimen to be measured disposed between two polarizers is measured by an orthogonal Nicol optical system which comprises a light source, said two polarizers, and a light receptor which are uniaxially arranged, thereby determining the optical axis direction of the specimen to be measured, characterized by conveyor means for continuously feeding and removing said specimen to be measured to and out of an optical axis in the longitudinal direction, said conveyor means being disposed to intersect with the direction at a right angle, in which said orthogonal Nicol optical system is disposed, a casing for said apparatus being such a shading case as to cover said orthogonal Nicol optical system as a whole, said specimen to be measured being adapted to pass through said casing for movement.

According to the invention, an apparatus for continuously measuring an optical axis direction is characterized by being composed of an orthogonal Nicol optical system, drive means for intersecting a specimen to be measured with an optical axis of said optical system at a right angle to continuously move said system, a reference specimen holder for intersecting a reference specimen, used for presenting a reference value with said optical axis at a right angle, to hold said specimen, and an external operative mechanism for extending an operative knob out of a casing to rotate said holder around said optical axis upon rotatable operation of said knob.

An apparatus for measuring a displacement from an absorption axis comprises an orthogonal Nicol optical system which uniaxially arranges a light source, two polarizers, and a light receptor, and rotary means for a reference specimen adapted to rotate the reference specimen with the same intersecting with the Nicol optical system at a right angle, and is characterized in that the angle of displacement from an absorption axis of the specimen to be measured is measured by a relation between intensity of the light transmission to the specimen to be measured provided between the two polarizers, intensity of the transmissive light on the reference specimen and the angle of deviation from the absorption axis.

The invention may be designed so that a specimen to be measured disposed between two polarizers is rotated around an axis of an orthogonal Nicol optical system to measure intensity of the transmissive light by the orthogonal Nicol optical system which unidirectionally arranges a light source, the two polarizers, and a light receptor, and that an angle of rotation to a position of rotation, where intensity of the transmissive light is at the minimum, thereby measuring deviation of the absorption axis of the specimen to be mesured.

DETAILED DESCRIPTION OF THE PREFERRED EMBODIMENTS

The invention will now be described in conjunction with the accompanying drawings.

Figure 1:
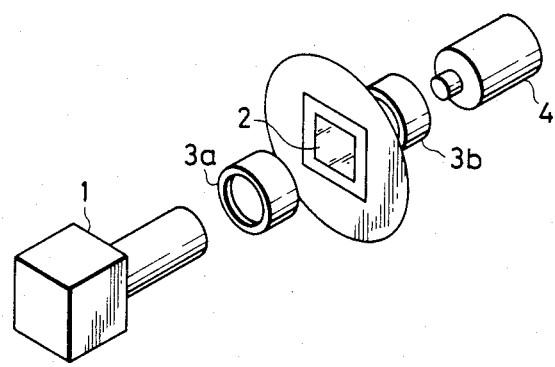
FIG. 1 is a perspective view of a prior art apparatus for measuring a polarizing property of a specimen.
Figure 1A:
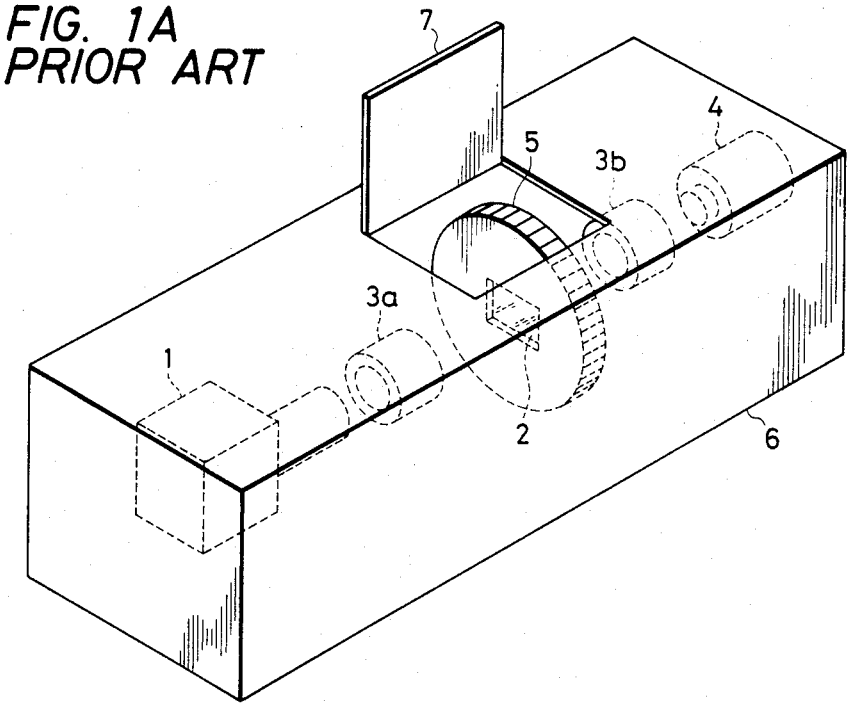
FIG. 1A is the prior art apparatus, shown in FIG. 1, provided with a casing.
Figure 1B:
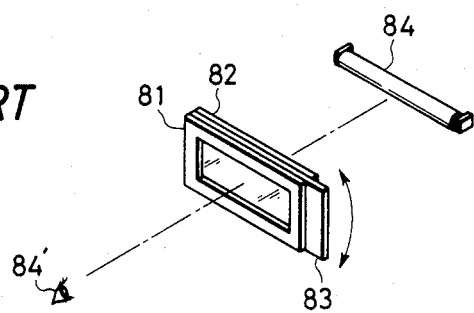
FIG. 1B is a perspective view of a conventional apparatus for measuring an absorption axis of the specimen.
Figure 2:
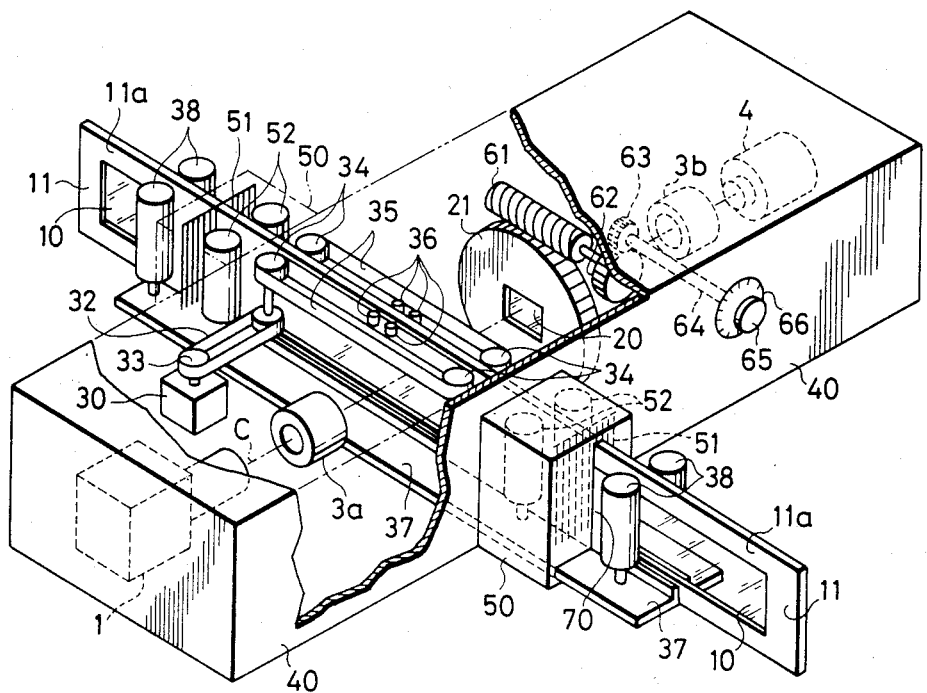
FIG. 2 is a partially fragmentary perspective view showing an apparatus for continuously measuring a polarizing property of a specimen, such as an optical axis direction or light absorption axis in accordance with the present invention.

FIG. 2 is a perspective view of an embodiment of the invention with a casing partly broken away.

An orthogonal Nicol optical system is composed of a light source 1, two polarizers 3a, 3b disposed to intersect optical axes thereof with each other, and a light receptor 4. These components are uniaxially arranged as shown. A casing 40 is provided so as to cover the orthogonal Nicol optical system. Means for conveying a specimen to be measured is disposed in a direction intersecting with an optical axis C of the Nicol optical system at a right angle. Conveyor means comprises a motor (not shown) as a drive source thereof, a speed reducer 30, a transmission belt 32, pulleys 33, 34, conveyor belts 35, back-up rollers 36, guide rails 37, and guide rolls 38. The guide rails 37 are mounted to pass through the casing 40. A holder 11 to which the specimen 10 to be measured is conveyed along the guide rails 37. The specimen is conveyed in such a manner that a pair of the conveyor belts 35 abut against a frame 11a of the holder 11 on the opposite sides and hold the same therebetween. The backup rollers 36 aid in clamping the belts 35 to the frame. The guide rolls 38 are mounted in pairs outwardly of the casing 40 to maintain a position of the specimen holder 11. Each of shading hoods 50 is disposed at the inlet 70 and outlet into the casing 40 for the specimen 10 and are each provided therein with a shading screen 51 and shading rollers 52. The operator inserts the forward end of the holder 11 to which the specimen 10 is set, into the casing 40 along the guide rails 37. Then he may remove the holder 11 projected from the casing 40 upon completion of the measurement.

A reference specimen 20 is used to provide a datum value to a relationship between an intensity I of the transmissive light as measured with the specimen 10 and an angle $\phi$ of displacement from the optical axis. The reference specimen holder 21 is set before or after measurement of the specimen 10 and is placed on the optical axis C. The reference specimen holder 21 is rotated around the optical axis C by external operative means which comprises a worm 21, first and second gears 62, 63, a power transmission shaft 64, an operative knob 65, and a protractor 66 and the like.

Operation of measurement of the optical axis direction in the respective positions in the longitudinal direction of the specimen 10 to be measured by use of the instant apparatus will now be explained. The holder 11 to which the specimen 10 to be measured is set is inserted into the casing 40 on one side thereof along the guide rails 37 with the reference specimen 20 in an unset condition. The specimen 10 is conveyed by the conveyor means to continuously traverse the optical axis C of the Nicol optical system and is then removed out of the casing 40 on the other side thereof. This will measure the intensity I of the transmissive light in the respective positions in the longitudinal direction of the specimen 10. Next, the reference specimen 20 cut out from the same material in a lot as that of the specimen 10 is set in the holder 21 and is rotated by external operative means around the optical axis C to measure the intensity I of the transmissive light. A relationship between the intensity I of the transmissive light and the angle $\phi$ of displacement between the optical axes of the specimens 10, 20 (an angle of displacement from the optical axis of the polarizer 3a to the optical axes of the specimens 10, 20) is established as expressed in the following formula:

$$I \propto \sin^2(2\phi)$$

The reference specimen 20 provides a point of I=0 with its rotation through an angle of at least 90°. This is the point where the angle $\phi$ of displacement is formed. Therefore, the reference specimen 20 causes the angle $\phi$ of displacement to correspond to the intensity I with the ratio of 1:1. For this reason, the intensity I of the transmissive light in the respective positions of the specimen 10 is made to be related to the intensity of the reference specimen 20 to determine the angle $\phi$ of deviation in the respective positions of the specimen 10 to be measured.

According to the invention, the conveyor means for continuously moving the specimen to be measured is disposed in a direction intersecting with the uniaxially arranged orthogonal Nicol optical system at a right angle so that the elongated specimen, as it is, may be continously measured in the longitudinal direction thereof without cutting the specimen into short segments. Further, it is enough to insert the specimen to be measured into the casing on one side thereof and remove it from the casing on the other side thereof, thereby rendering operation very simple and smooth. In general, measurement of the specimen to be measured in the optical axis direction may be quickly and continuously conducted.

As described above, the optical axis measuring apparatus which comprises the orthogonal Nicol optical system, specimen conveyor means, and external operative means and the like should be fabricated to prevent the exterior light from entering since an entrance of the light from those other than the light source renders measurement inaccurate. As is different from the conventional apparatus, the instant apparatus is designed to arranged the conveyor means so as to intersect with the direction with a right angle in which the Nicol optical system to thus continuously measure the elongated specimen to be measured. In such a case, an attempt may be made to use the casing 40 to cover the apparatus as a whole to prevent the exterior light from entering. This would increase the weight of the apparatus and would also elongate a powder transmission shaft 64 of the external operative means. According to the invention, the casing 40 is fabricated in the form of a shading casing to cover the entire orthogonal Nicol optical system on one hand, and guide rails 37 and rolls 38 are exposed to the exterior of the casing 40 through which the elongated specimen to be measured passes for feed and removal. Thus, the invention is intended to provide the shading hoods 50 in positions corresponding to the inlet 70 and outlet of the specimen to be measured, the hoods being each provided therein with the shading screen 51 and the shading rollers 52 to prevent the exterior light from entering.

The orthogonal Nicol optical system and conveyor means are crosswise intersected with each other at a right angle, the casing for the apparatus is designed in the form of such shading casing as to cover the entire orthoginal Nicol optical system and to have the specimen to be measured passed through the casing for movement so that the apparatus as a whole may be light in weight and compact in structure. In addition, the arrangement of operative means for operating the internal mechanism from outside of the casing is simplified and reliable because of a short distance between the casing and the internal mechanism.

Figure 3:
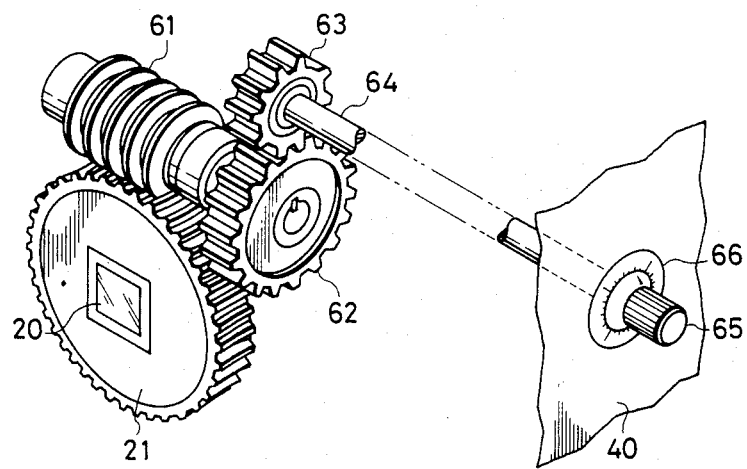
FIG. 3 is a perspective view of an operation means incorporated into the apparatus shown in FIG. 2.

As best shown in FIG. 3, the reference specimen 20 is held in a reference specimen holder 21 so as to intersect with the optical axis C at a right angle. The holder 21 is geared on its outer periphery and adapted to be driven by the external operative mechanism. In FIG. 3, the externally operative mechanism comprises a worm 61 meshing with the holder 21, a first gear 62 fixed coaxially with the worm 61, a second gear 63 meshing with the first gear 62, and a power transmission shaft 64 one end of which the gear 63 is fixed to. The operative knob 65 is fixed to the other end of the shaft 64 which extends from the casing. The protractor 66 formed on the knob 65. The knob 65 is rotated with the protractor 66 to rotate the holder 21 by an angle correcponding to the degree indicated by the protractor.

For measurement using the mechanism shown in FIG. 3, the specimen 10 to be measured is initially mounted on a first holder 11 to insert its one end into the casing 40. The first holder 11 is then moved at a constant speed by conveyor belts 35 to continuously measure intensity of the transmissive light. At this moment, the reference specimen 20 is not yet set in a position in the holder 21. A relation between intensity I of the transmissive light and an angle $\theta$ of optical axis, namely an angle of deviation from an angle of optical axis direction of the polarizer 3a and another optical axis direction each of parts of the specimen 10 may be expressed in the following formula:

$$I \propto \sin^2(2\phi)$$

In this connection, it is noted that at this stage the intensity I is varied in response to change in the angle $\theta$ of deviation but the actual angle $\theta$ of displacement is not known. Accordingly, the reference specimen 20 is mounted on the holder 21 and rotated to thereby measure the intensity of the transmissive light at which time the specimen 10 is removed. The reference specimen 20 to be used is manufactured from material in the same lot so that an an irregularity in thickness of material and an error in refractive index may be avoided. An angle through which the reference specimen 20 rotates may be at least 90°. Rotation of the reference 20 is made by rotatably operating the operative knob 65. Since the angle $\phi$ of displacement is at 0° through the 90°-angular rotation of the specimen 20, it is understood therefrom that the angle $\phi$ of deviation is positioned at 0° where intensity of the transmissive light is at the minimum. Now, the knob 65 is positioned to set it to the 0-scale on the protractor and is then rotated to hold 1°, 2°, 3°, . . . for obtaining the respective datum values. For this reason, the relation between the angle $\phi$ of deviation derived from the reference specimen and the intensity I of the transmissive light at this point is applied to the specimen 10 as previously measured to determine the angle $\phi$ of displacement originated from the optical axis in the respective positions of the specimen 10 being moved in the longitudinal direction.

According to the invention, the continuous measuring apparatus is arranged so that the reference specimen is rotated by rotation of the operative knob positioned out of the casing to thus avoid occurrence of error in measurement caused by the entering light due to opening and closing of the cover, thereby improving an accuracy of measurement. As compared with the conventional apparatus which have been heretofore operated by opening and closing the cover, the instant apparatus is smooth and quick in operation. A ratio of rotation between the operative knob and the holder is suitably set to roughly but finely adjust an angle with accuracy through which the reference specimen is rotated, as compared with the conventional apparatus adapted to manually and directly rotate the reference specimen.

Figure 4:
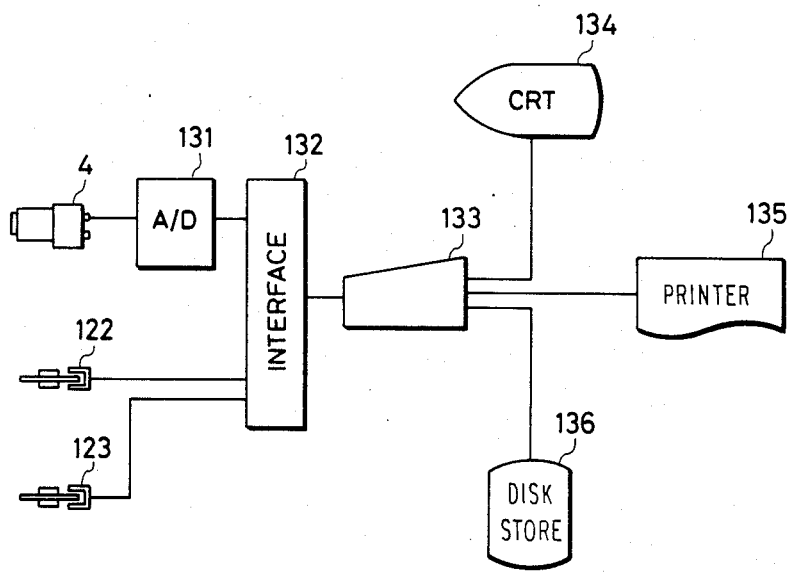
FIG. 4 is a diagram of a processor for an automatic continuous measuring system in accordance with the present invention.

The invention will be explained in conjunction with FIG. 4. The angle $\phi$ of displacement from the absorption axis may be automatically measured and displayed. FIG. 4 is a block diagram showing one form of automatic display means. The light receptor 4 described before is in the form of a photo-multiplier. Detector means is composed of the photo-multifier 4 and two rotary encoders 122, 123. The photomultifier 4 is adapted to detect intensity of the transmissive light in the orthogonal Nicol optical system. This intensity is inputted through an A/D converter 131 and an interface 132 to a microcomputer 133 which is available on the market as PC8801 made and sold by Nippon Electric Co., Ltd. and Apple II made by Apple Co. The two rotary encoders 122, 123 contact the specimen holder 11 and the reference specimen holder 21, to represent the amount of movement of the holder 11 and the amount, or rotation of the holder 21. These amount are inputted as a displacement pulse by the interface 132 to the microcomputer 133. The microcomputer 133 compare information from the photomultifier 4 with information from the rotary encoders 122, 123 to determine the angle of displacement from the absorption axis in the respective positions in the specimen. The angle $\phi$ of displacement displayed as an image in a CRT 134. A printer 135 and a magnetic disc 136 are connected to the microcomputer 133 to print out and store the data. Automatic display means shown in FIG. 4 requires no manual rotary manipulation. Instead, drive means is provided to rotate the reference specimen holder 21 at a definite speed.

Operation of the automatic display will be further described hereinafter. The angle of rotation of the reference specimen 20 is detected by the rotary encoder 123 whereas the intensity of the transmissive light of the reference specimen 20 is detected by the photomultifier 4 to input them to the computer, thereby having the angle $\phi$ corresponded to the intensity I of the transmissive light in advance.

Next, the reference specimen 20 is removed whereas the specimen 10 to be measured is set to the holder 11 and is continuously moved by specimen movable means in a direction intersecting with the optical axis C to continuously measure the intensity I of the transmissive light in the respective positions. The intensity of the transmissive light is detected by the photomultifier 4 and inputted to the computer 133. On the other hand, the amount of the specimen 10 to be measured is detected by the rotary encoder 122 and then inputted to the computer 133. In the computer 133, a scale in the longitudinal direction of the specimen is determined by the speed of movement of the specimen to be measured, and the angle $\phi$ which corresponds to the intensity I of the transmissive light, obtained from the specimen 10 to be measured, is provided by a relationship between the angle $\phi$ of the reference specimen 20 and the intentisty I of the transmissive light (since the specimen 10 to be measured and the reference specimen 20 are the same in quality and thickness, the proportion constant A is common to both the specimens). The scale in the axis of ordinate is determined by the angle $\phi$ of displacement from the absorption. The image in which the abscissa is put as the longitudinal position of the specimen 10 to be measured and the ordinate is put as the angle $\phi$ is outputted to the CRT. The image is also outputted by change-over operation to a printer 135 and a magnetic disc 136. In displaying the image, a specimen number is inputted and expressed in the image simultaneously with result of measurement.

According to the invention, if a relation between the angle of displacement from the absorption axis and the intensity of the transmissive light is previously obtained through the reference specimen, the angle of displacement may be known from only measurement of the intensity of the transmissive light in measuring the specimen to be measured. Consequently, measurement may be very quickly made without measuring an angle everytime. The intensity of the transmissive light is measured by use of the light receptor to provide accurate measurement as is different from observation through the eye. Since the specimen to be measured is not required to rotate to a position of measurement, continuous measurement may be made in the respective positions of the specimen to be measured. Where such the apparatus is adapted so that the specimen to be measured is continuously fed and removed by conveyor means disposed in a direction intersecting with the orthogonal Nicol optical system, the angle of displacement from the absorption axis may be contiuously measured in the longitudinal direction of the specimen as it is without cutting it into short segments even if it is elongated. For the orthogonal Nicol optical system and conveyor means intersecting therewith, the casing for the apparatus is fabricated in the form of a shading casing sufficient to cover the orthogonal Nicol optical system to feed the specimen to be measured to the casing one side thereof and remove it out of the casing on the other side thereof so that the apparatus as a whole may be very light in weight and compact in structure. In addition to the Nicol optical system, conveyor means, reference specimen rotary means, there may be provided detector means for detecting the intensity of the transmissive light, moving distance, and angle of rotation as well as display means for processing information from detector means and for outputting the angle of deviation from the absorption axis of the specimen to be measured to express it in the image so that the result of measurement is visually determined at once to facilitate inspection of the products and the like.

Figure 5:
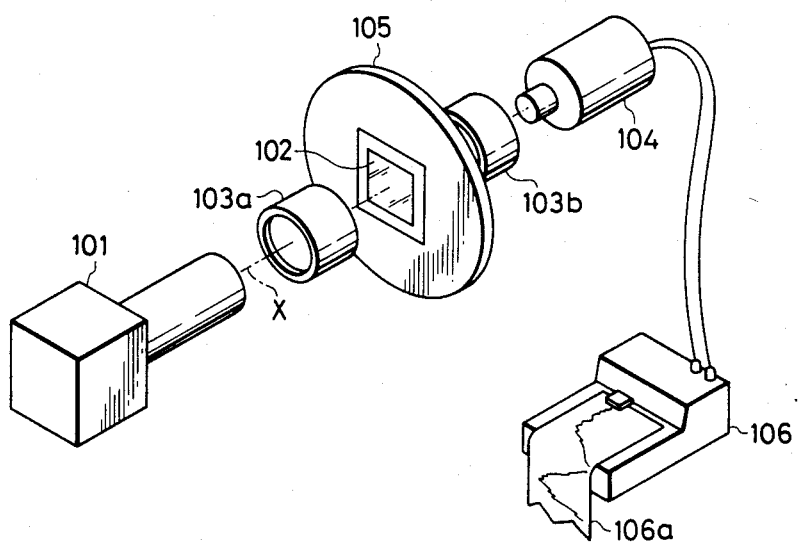
FIG. 5 is a perspective view showing an apparatus for carrying out a method according to the invention.

FIG. 5 is a perspective view of an apparatus for carrying out a method according to the invention. An orthogonal Nicol optical system is composed of a light source 101, two polarizers 103a, 103b disposed to intersect absorption axes with each other at a right angle, and a light receptor 104. A specimen 102 to be measured in a chip form is so inserted as to intersect the surfaces with an axis X of the Nicol optical system and is rotated around the axis X to have the transmissive light caught in the respective positions of rotation, thereby measuring intensity of the transmissive light. Numeral 105 designates a holder. Intensity of the transmissive light may be written with a pen by use of a recorder 106. In this case, it is noted that a speed at which a paper 106a is moved is adapted to correspond to an angular speed at which the specimen 102 is rotated.

Now, the operation of measuring an angle $\phi$ of displacement from the absorption axis of the specimen 102 to be measured will be explained hereinafter.

The specimen 102 is inserted between the polarizers 103a, 103b whereas parallel rays are irradiated from the light source 101 to catch the transmissive light by the light receptor 104 at which time intensity of the transmissive light may be expressed in the following formula:

$$I = A^2 \sin^2(2\phi) \cdot \sin^2(\delta/2)$$

where
$\delta = 2\pi \cdot \Delta n \cdot d / \lambda$
A: constant
$\phi$: angle of deviation from absorption axis
$\delta n$: difference in refractive index
d: thickness of specimen to be measured
$\lambda$: wavelength of light source In this connection, it is noted that $\Delta n$, d, and $\lambda$ are not varied so long as the apparatus and the specimen are always the same. The intensity I of the transmissive light becomes solely a function of the angle $\phi$ of displacement from the absorption axis. Namely, as described before, it is expressed in the following.

$$I \propto \sin^2(2\phi)$$

Accordingly, theoretically speaking, the angle $\phi$ of rotation to a point where the intensity of the transmissive light would be zero is the angle $\phi$ of displacement from the absorption axis of the specimen 2 to be measured. However, there may be actually a noise so that the angle $\phi$ of rotation to a position of rotation, where the intensity of the transmissive light is at the minimum, may be determined to be the angle $\phi$ of displacement from the absorption axis. If a relationship between the intensity of the transmissive light and the angle of displacement is expressed by use of the recorder, the angle $\phi$ from the absorption from the specimen 2 to be measured may be instantly and visually observed. When it is desired that the angle $\phi$ from the absorption axis each of a plurality of the specimens manufactured from the same rods, a relation between the intensity of the transmissive light and the angle $\phi$ from the absorption axis is previously known by rotation of one specimen so that the value of corresponding angle $\phi$ of deviation from the absorption axis may be known by only measuring the intensity of transmissive light in that position without rotation of the other specimens to be measured.

According to the invention as above consituted, the angle of deviation from the absorption axis of the specimen to be measured may be readily known without fail. Moreover, measurement is also quickly made to thus apply the instant method to qualify the control of the polarizer and production control thereof.

What is claimed is:

1. An apparatus, for continuously measuring in a longitudinal direction the polarization axis of a first specimen having a planar surface and being substantially elongated in said longitudinal direction such that the polarization axis of said first specimen may vary significantly with said direction, said apparatus having an orthogonal Nicol optical system that includes a source of illumination, first and second polarizers, and a light receptor disposed along a single optical axis, the polarization axis of each of said first and second polarizers being orthogonal with respect to the other, the improvement comprising, moveable means adapted to transport the planar surface of said first specimen between said first and second polarizers and in a direction across and perpendicular to the single optical axis, and to identify the location of the optical axis as a function of length along said planar surface, rotatable means disposed between said first and second polarizers and adapted to hold a second specimen in a position orthogonal to the single optical axis and to rotate said specimen about an axis substantially coincident with said single optical axis, and to measure the angle of rotation as a function of the intensity of light detected by said receptor, and means responsive to said measured angle of rotation from said rotatable means as a function of intensity measured by said receptor means, and responsive to said measured intensity of light as a function of length along the planar surface of said first specimen when conveyed by said moveable means, to determine said polarization axis as a function of length along said first specimen.

2. A measuring apparatus as claimed in claim 1 wherein said rotatable means comprises an external operative mechanism for extending an operative knob out of a casing to rotate said holder around said optical axis upon rotatable operation of said knob.

3. A measuring apparatus as claimed in claim 1 wherein the angle of displacement from an absorption axis of the specimen to be measured is measured by a relationship between an intensity of the light transmissive to the specimen provided between the two polarizers, the intensity of the transmissive light on the reference specimen and the angle of displacement from the absorption axis.

4. The apparatus according to claim 3, wherein conveyor means for continuously feeding and removing the specimen to be measured to an out of the orthogonal Nicol optical system is disposed to intersect at a right angle with the single optical axis in which the Nicol optical system is arranged.

5. The apparatus according to claim 4 wherein a casing for the apparatus is in the form of a shading casing sufficient to cover the orthogonal Nicol optical system, and wherein the specimen to be measured is supplied by said moveable means to the casing on one side thereof and removed out of the casing on the other side thereof.

6. The apparatus according to claim 5, wherein shading means is disposed at the inlet and outlet into the casing for the specimen to be measured to prevent the light from entering.

7. The apparatus according to claim 3, wherein the moveable means comprises a conveyor means for continuously moving the specimen to be measured to intersect with the optical axis of the Nicol optical system at right angle, and further includes detector means for detecting the intensity of the transmissive light, a moving distance of said specimen, and an angle of rotation with respect to the specimen and the reference specimen, and display means for processing information from said detecting means for outputting the angle of displacement in an image form from the absorption axis of the specimen to be measured.

8. A method for continuously measuring the absorption axis of an object specimen that is substantially elongated in a longitudinal direction such that the polarization axis of said object specimen may vary significantly with said direction, comprising the steps of, establishing a uniaxial Nicol system having along a common optical axis a source of light, two polarizers having their axis of polarization orthogonal to each other and a light intensity detector, rotating a reference specimen, having common optical properties to said object specimen and being disposed between said two polarizers, around said common optical axis in a plane normal to said axis, measuring and recording the intensity of transmissive light as a function of the angle of rotation of said reference specimen and, in particular, measuring and recording the angle of rotation to a position of rotation where intensity of transmissive light is at a minimum, continuously moving said object specimen between said two polarizers and across said common optical axis in a plane normal to said axis, measuring the intensity of transmissive light as a function of distance along said object specimen, and continuously comparing said measured and recorded light intensity for different angles of rotation of said reference specimen with said measured light intensity as a function of distance along said object specimen in order to measure the angle of displacement of the absorption axis of said object specimen as a function of distance along said object specimen.

* * * * *